United States Patent [19]

Ritter et al.

[11] Patent Number: 5,280,018
[45] Date of Patent: Jan. 18, 1994

[54] VEHICLE FOR OPTICAL APPLICATION OF PHARMACEUTICALS

[75] Inventors: Lawrence Ritter, Suffern; James R. Lawter, Goshen, both of N.Y.

[73] Assignee: American Cyanamid Company, Wayne, N.J.

[21] Appl. No.: 377,590

[22] Filed: Jul. 10, 1989

Related U.S. Application Data

[60] Division of Ser. No. 145,451, Jan. 19, 1988, Pat. No. 4,889,845, which is a continuation of Ser. No. 870,392, Jun. 9, 1986, abandoned.

[51] Int. Cl.$^5$ .................... A61K 7/06; A61K 9/12; A61K 31/695
[52] U.S. Cl. ......................... 514/63; 424/47; 514/880
[58] Field of Search ............................ 514/63

[56] References Cited

U.S. PATENT DOCUMENTS

| | | | |
|---|---|---|---|
| 4,472,375 | 9/1984 | Bohieh, Jr. et al. | 424/70 |
| 4,552,755 | 11/1985 | Randen | 424/81 |

FOREIGN PATENT DOCUMENTS

| | | | |
|---|---|---|---|
| 2615654 | 10/1977 | Fed. Rep. of Germany | 514/63 |
| 48-19941 | 6/1973 | Japan | 514/63 |
| 53-142542 | 12/1978 | Japan | 514/63 |
| 0803289 | 10/1958 | United Kingdom | 514/63 |
| 0875780 | 8/1961 | United Kingdom | 514/63 |

OTHER PUBLICATIONS

*Current Therapy,* pp. 599–601 (1984).

*Primary Examiner*—Dale R. Ore
*Attorney, Agent, or Firm*—James V. Costigan

[57] ABSTRACT

A topical pharmaceutical formulation, useful as a vehicle for E-type prostaglandins and in the treatment of androgenetic alopecia, is described.

2 Claims, 5 Drawing Sheets

VEHICLE FOR OPTICAL APPLICATION OF PHARMACEUTICALS

This is a divisional application of U.S. patent application Ser. No. 07/145,451, filed Jan. 19, 1988, now U.S. Pat. No. 4,889,845, which is a continuation of Ser. No. 06/870,392 filed Jun. 9, 1986, now abandoned.

BACKGROUND OF THE INVENTION

Prostaglandins are a group of cyclic fatty acids that possess diverse and potent biologic activities affecting cellular function in every organ system. The parent compound, prostanoic acid, contains a 20 carbon chain with a cyclopentane ring.

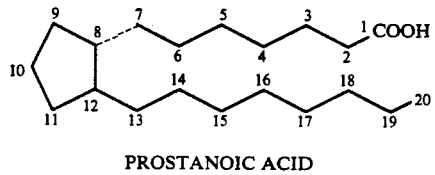

PROSTANOIC ACID

Variations in the number and position of the double bonds and hydroxyl groups determine the physiologic activities of the various prostaglandins.

Conventionally, prostaglandins are divided into types E, F, A, B, C and D based on functions in the cyclopentane ring. Numerical subscripts refer to the number of unsaturations in the side chains-and $\alpha$ or $\beta$ subscripts refer to the configuration of the substituents in the ring. The naturally occurring prostaglandins are types E, F, A and B. All naturally occurring prostaglandins have a trans 13,14 position bond and an hydroxyl group at $C_{15}$.

The E- and F-type prostaglandins possess an additional hydroxyl at $C_{11}$. At $C_9$, E-type prostaglandins have a carbonyl function while F-type prostaglandins have an hydroxyl. In general, A- and B-type prostaglandins may be regarded as dehydration products of E-type prostaglandins; i.e., the removal of the $C_{11}$ hydroxyl and the formation of a double bond in the cyclopentane ring.

The known biologic activities of prostaglandins of the E-type include activities as hypotensive agents, bronchodilators, and gastric acid secretion inhibition agents. [Bergstrom, et al., PHARMACOL., REV., 20:1 (1968) ]. However, pharmaceutical use of E-type prostaglandins has been impeded by their instability. E-type prostaglandins generally decompose slowly at room temperature and above, which decomposition is accelerated in the presence of small amounts of acid or base. Accordingly, E-type prostaglandins are unstable in pharmaceutical formulations containing water or hydroxylic compounds. Even in neutral, aqueous solution or in neat state there is a gradual decomposition of E-type prostaglandins to A- and B-type prostaglandins.

Good stability of the E-type prostaglandins has been observed in some solutions and in pure form at temperatures of −20° C. or lower. However, storage at such temperatures is impractical. Some success at stabilization at room temperature has been reported when non-alcoholic compounds such as ethyl acetate and chloroform are employed as solvents for E-type prostaglandins. Such solvents, however, are unsuitable for pharmaceutical dosage applications.

More recently, good stability of E-type prostaglandins was reported with use of triethyl citrate as a solvent (U.S. Pat. No. 4,211,793) and with use of hydroxylated derivatives of fatty acids (U.S. Pat. No. 4,431,833).

Although hair serves no vital function in humans, the psychological impact from excess hair growth or loss of hair can be enormous. For some men in particular, as a result of aging and predisposing genetic factors, scalp baldness occurs in stages often resulting in a complete loss of scalp hair. This baldness is known as male pattern baldness or androgenetic alopecia. It is believed that an accumulation of 5-α-dihydro testosterone, a tissue-active androgen, in some scalp hair follicles over time causes the regression of hair growth in such follicles. However, androgen production is no higher in men with androgenetic alopecia than in those with full scalps of hair.

There is no effective treatment for androgenetic alopecia at the present time. There have been some reports that minoxidil, a potent vasodilator, has been effective in causing scalp hair growth in patients with androgenetic alopecia. However, contrary to some popular belief, there is no evidence of a vascular deficit to the scalp in patients with androgenetic alopecia.

THE INVENTION

It has been discovered that a formulation of: (1) polydimethylsiloxane (20 to 1,000,000 centistokes viscosity); (2) $C_{12}$–$C_{15}$ alcohols benzoate, isopropyl palmitate, isopropyl myristate, diisopropyl adipate, octyl hydroxystearate, PPG-2 myristyl ether propionate, almond oil or mixtures thereof; and (3) volatile silicones such as octamethylcyclotetrasiloxane, decamethylcyclopentasiloxane, hexamethyldisiloxane and other low molecular weight polydimethylsiloxanes and/or pharmaceutically acceptable chlorofluorocarbons; is useful in the treatment of androgenetic alopecia. It has also been determined that such formulation provides a vehicle for stable-storage of E-type prostaglandins.

In its broadest sense the formulation of the present invention may be described as:

| Ingredient | Concentration (% by weight) |
| --- | --- |
| Polydimethylsiloxane (20 to 1,000,000 centistokes) | 1 to 50 |
| Solvent 1* | 2 to 60 |
| Solvent 2** | 100 |

*Solvent 1 may be selected from esters such as $C_{12}$–$C_{15}$ alcohols benzoate, isopropyl palmitate, isopropyl myristate, diisopropyl adipate, octyl hydroxystearate, PPG-2 myristyl ether propionate, almond oil, etc.
**Solvent 2 may be selected from volatile silicones such as octamethylcyclotetrasiloxane, decamethylcyclopentasiloxane, hexamethyldisiloxane and other low molecular weight polydimethylsiloxanes such as Dow Corning 200 Fluid 1.0 centistokes and 1.5 centistokes and pharmaceutically acceptable chlorofluorocarbons (such as the Freons).

In a specific sense, the composition according to the present invention may be described by the following formula:

| Formulation A | |
| --- | --- |
| Ingredient | Concentration (% by weight) |
| Polydimethylsiloxane (12,500 centistokes) | 15 |
| $C_{12}$–$C_{15}$ Alcohols Benzoate | 20 |
| Cyclomethicone (Octamethylcyclotetrasiloxane qs to | 100 |

The following description details the preparation of a typical formulation encompassed by this invention.

Formulation A

| Ingredient | Concentration (% by Weight) | Quantity (mg/0.3 ml) |
|---|---|---|
| Polydimethylsiloxane (12,500 centistokes) | 15 | 43 |
| $C_{12}$–$C_{15}$ Alcohols Benzoate | 20 | 57.4 |
| Cyclomethicone (Octamethylcyclotetrasiloxane | qs | — |

The polydimethylsiloxane was placed in a suitable container. One half of the total quantity of cyclomethicone was added to the container and the contents were stirred until homogenous.

The $C_{12}$–$C_{15}$ alcohols benzoate was added to the polydimethylsiloxane-cyclomethicone mixture. The resulting mixture was then stirred until homogeneous.

The remaining portion of cyclomethicone was added and this final solution was stirred until homogeneous. The resulting Formulation A can then be placed into suitable containers.

Clinical studies using healthy, male volunteers (age: 18–65) with vertex baldness and some recession of front hairline were performed using the above-described Formulation A. A patch of bald or balding scalp in the crown or vertex region near the margin of existing hairline, approximately one inch in diameter, was observed for hair growth. The hairs on such location were counted at the beginning of the study, and re-counts were done periodically during the course of the study. All hair, including unpigmented vellus and pigmented intermediate and terminal hair, was counted, except as indicated hereinbelow. The amount of Formulation A applied was approximately 3 ml, which amount was applied once daily to the bald and balding areas of the scalp. Formulation A was applied with an index finger and rubbing action. The volunteers were instructed to apply Formulation A to a clean and dry scalp. The chart below summarizes the results after three months of study.

| | Intermediate and Terminal Hair | Total Hair Count |
|---|---|---|
| Percent Increase in Hair from Initial Hair Count at Beginning of Study | | |
| >10% | 70% | 72% |
| >20% | 63% | 69% |
| >30% | 63% | 62% |
| >50% | 53% | 45% |
| >70% | 50% | 28% |
| >100% | 23% | 17% |
| >150% | 17% | 7% |
| >200% | 13% | 3% |
| >300% | 0% | 0% |

BRIEF DESCRIPTION OF THE DRAWINGS

Additionally, as the study proceeded beyond three months, the results were charted as mean hair counts over time.

Figure 1:
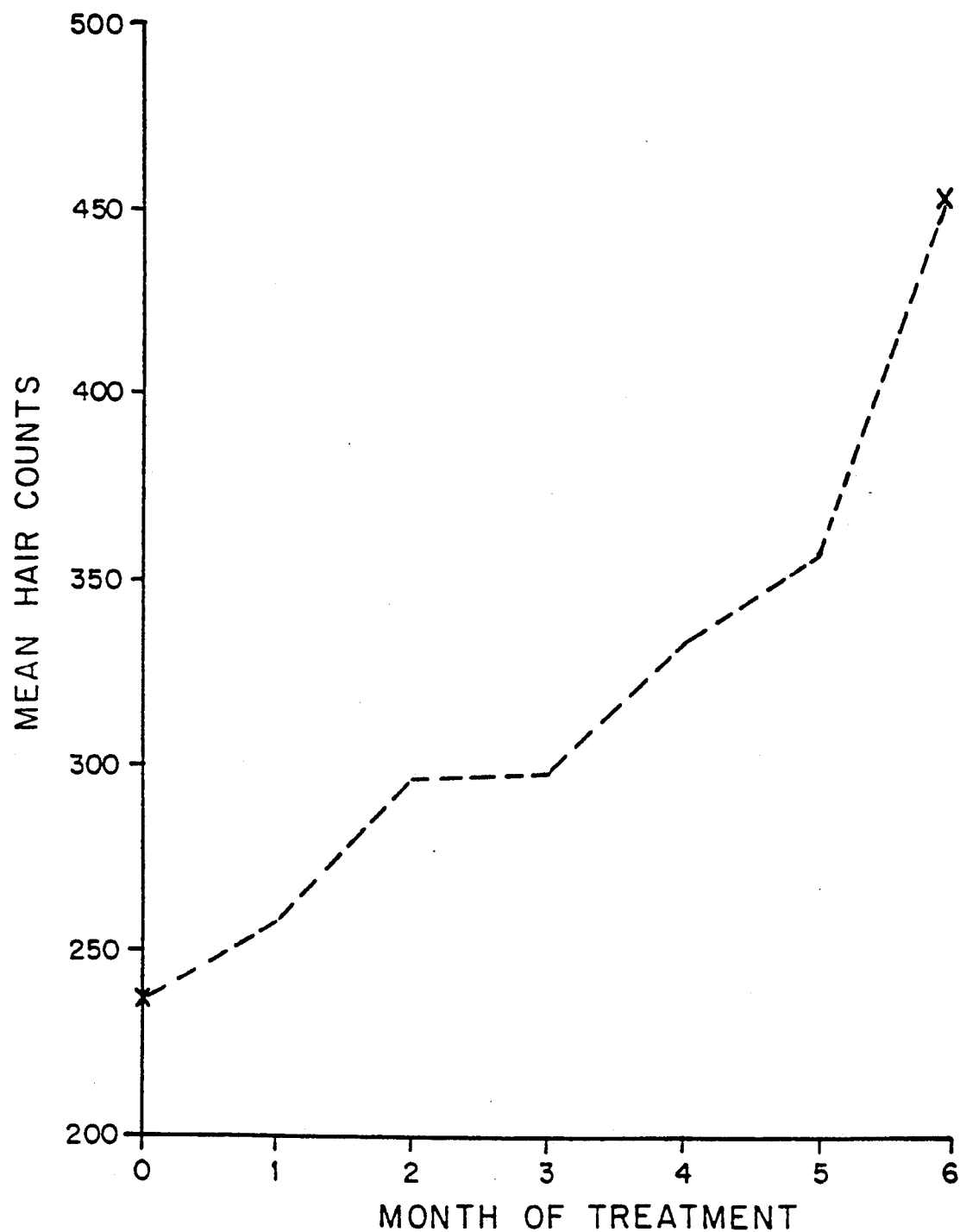
FIG. 1 shows the total mean hair count over a six-month period of time.
Figure 2:
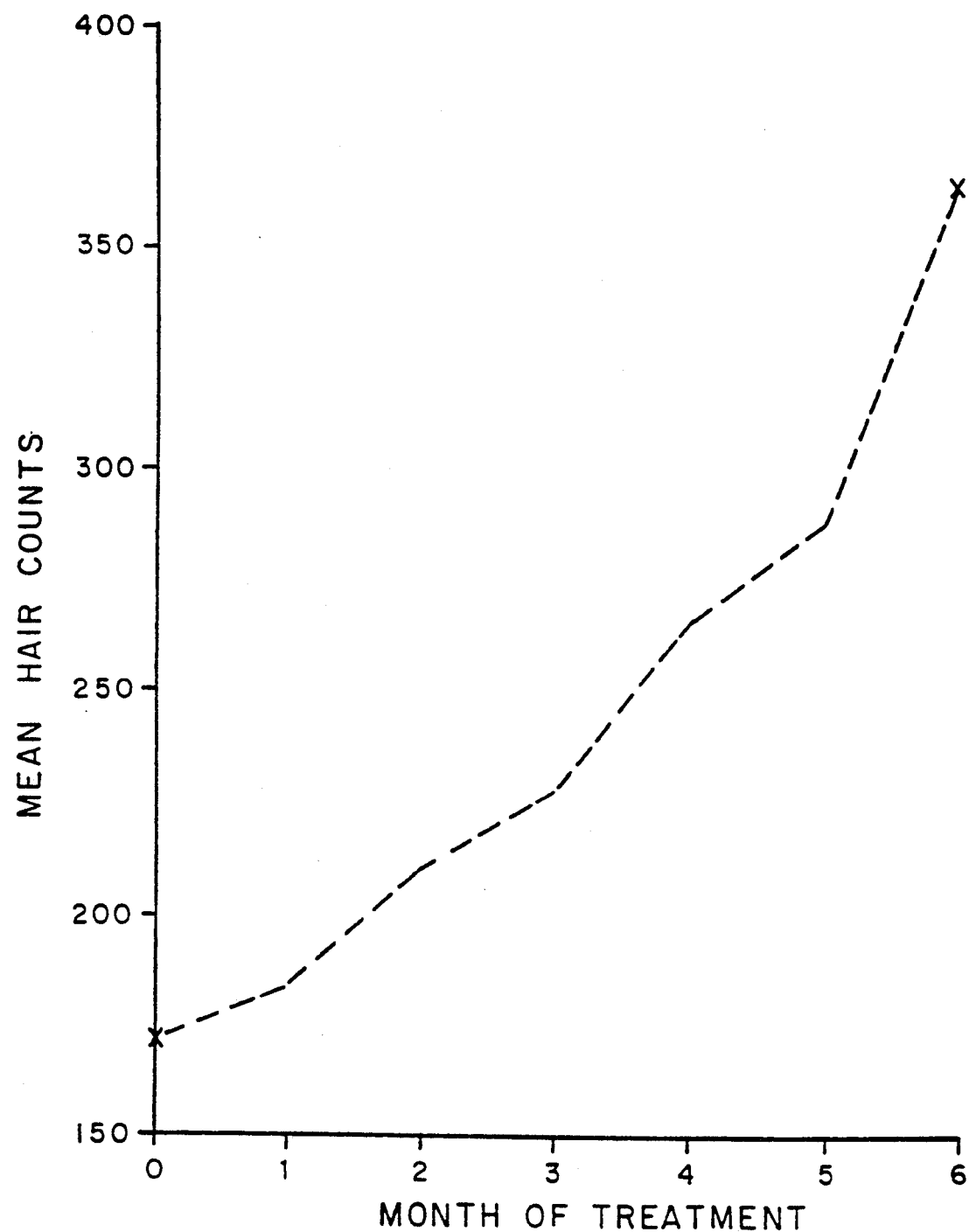
FIG. 2 shows the mean hair count of intermediate and terminal hair over a six-month period of time.
Figure 3:
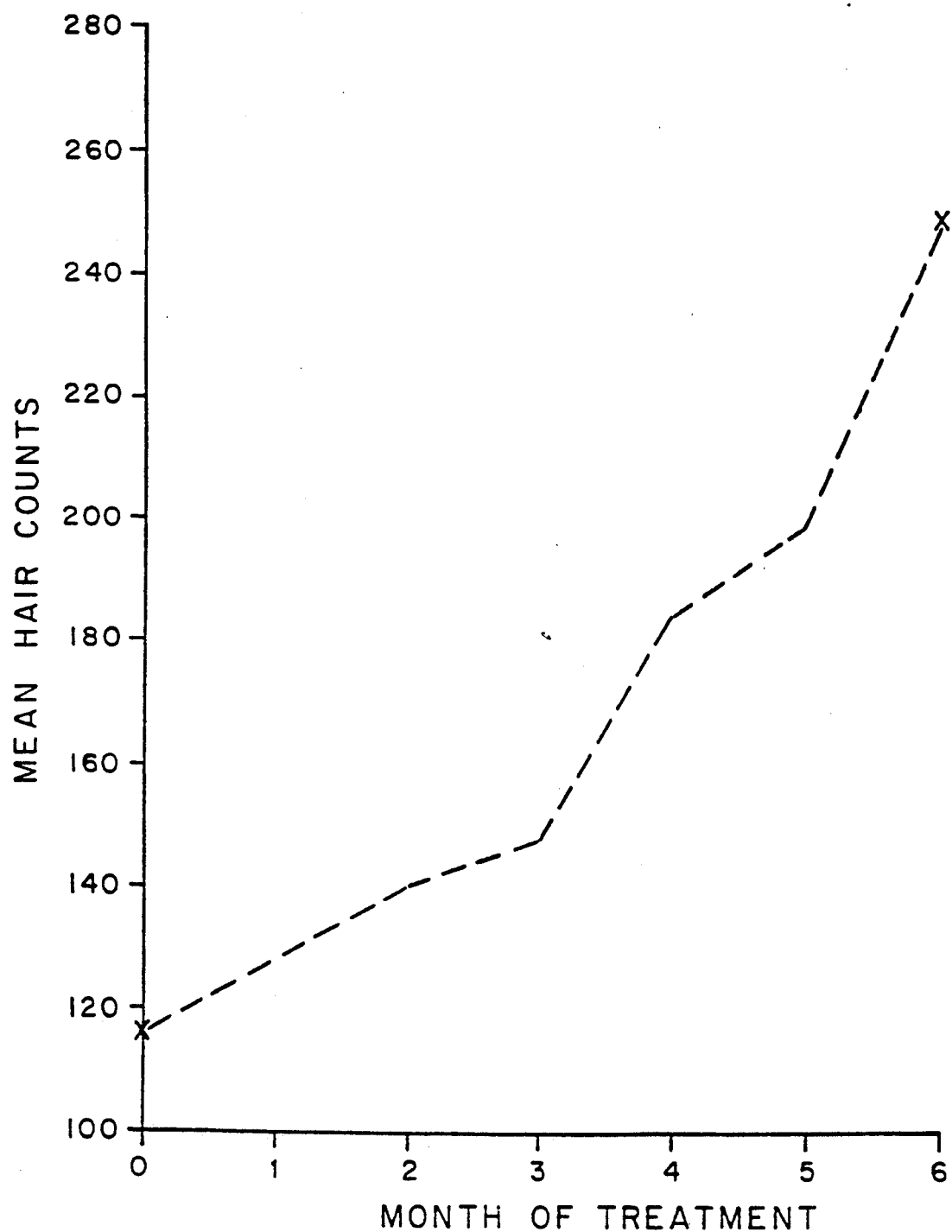
FIG. 3 shown the mean hair count of intermediate hair over a six-month period of time.
Figure 4:
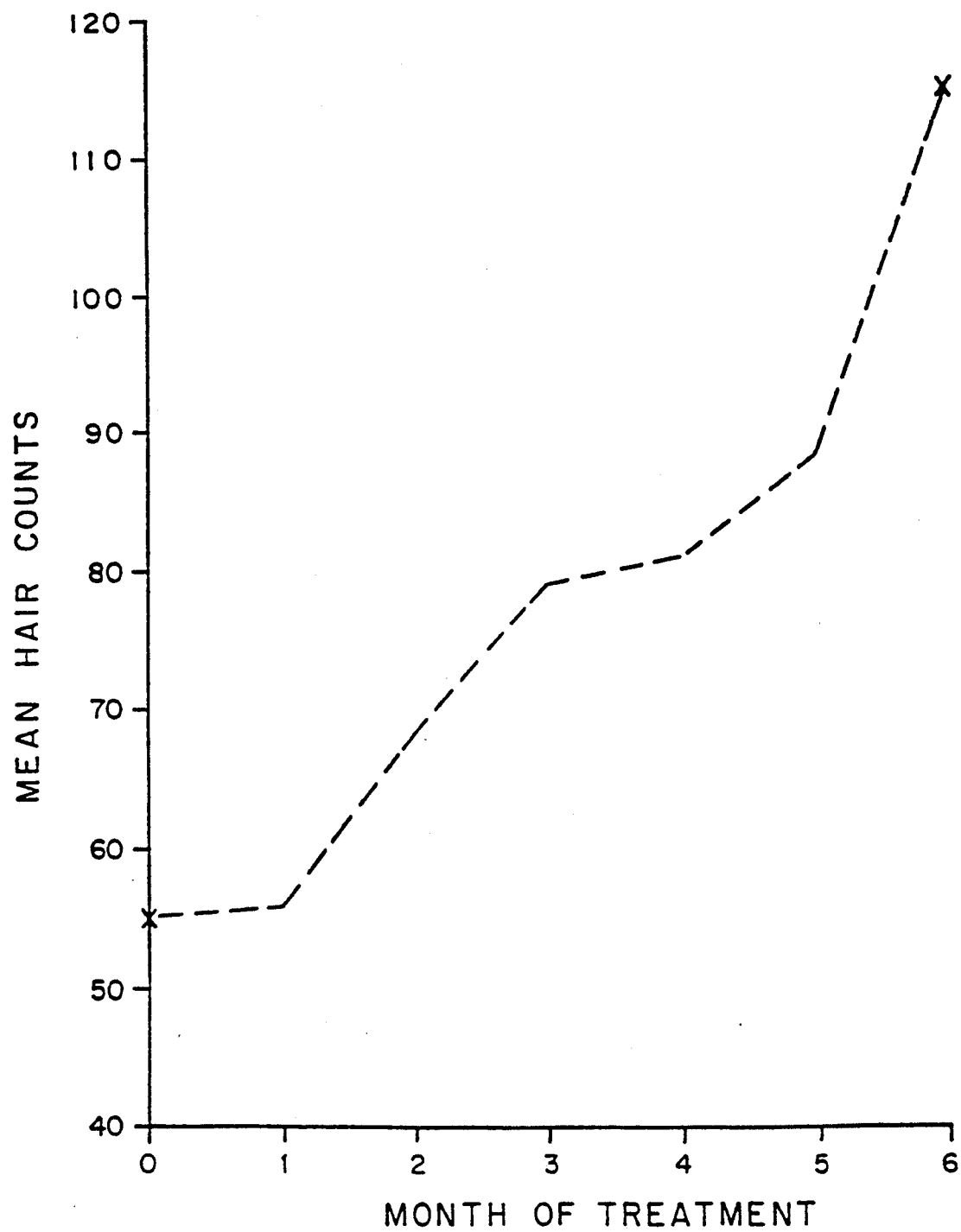
FIG. 4 shows the mean hair count of terminal hair over a six-month period of time.
Figure 5:
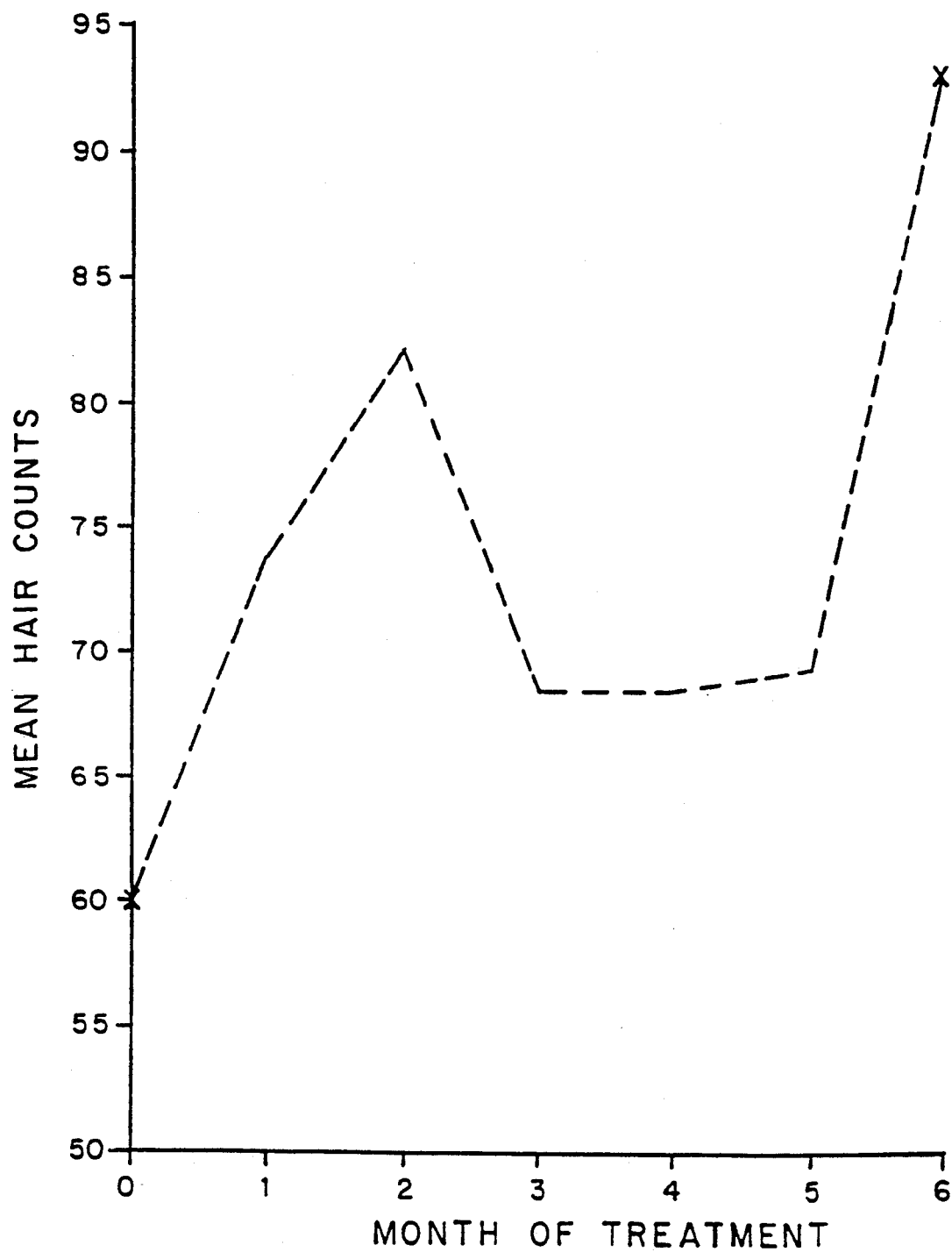
FIG. 5 shows the mean hair count of vellus hair over a six month period of time.

As is shown in the above chart and in FIGS. 1 through 5, topical application of Formulation A causes hair growth. The mechanism by which such formulation causes such growth is unknown. However, one proposed mechanism is that the ingredients clean hair follicles of accumulations of 5-α-dihydrotestosterone. If such proposal is correct, then it is believed that any of the three components of Formulation A would promote hair growth.

Additionally, the formulation of the present invention has been determined to be useful as a pharmaceutical vehicle for topical application of E-type prostaglandin. As more fully described hereinabove, a principal problem encountered with pharmacological utilization of prostaglandins resides in their relatively unstable nature in pharmaceutical formulations. The few successful attempts at providing stable formulations have resulted in oily liquid compositions such as the triethyl citrate formulation of U.S. Pat. No. 4,211,793. Such formulation is unsatisfactory for topical application, as such results in greasy build-up on the skin. Formulation A, it has been determined, presents a suitable vehicle for topical application of E-type prostaglandins. In particular, it presents a vehicle for topical application of viprostol, methyl (±) −[11α, 5Z (5E), 13 E, 16R and 16S ]-16 ethenyl-11,16-dihydroxy-9-oxoprosta-5, 13-dienloate, an E-type prostaglandin. Viprostol is active as an anti-hypertensive agent, inter alia, and can be used for such purpose with topical application. Formulation A and other formulations according to the present invention provide a non-greasy vehicle for topical application of viprostol. Additionally, viprostol may be dissolved in such vehicle without significant loss of its potency over extended periods of time at room temperature.

What is claimed is:

1. A method for treating androgenetic alopecia in male humans which method comprises topically applying to the affected scalp areas an effective amount of a composition comprising: 15 percent by weight polydimethylsiloxane, 20 percent by weight $C_{12}$–$C_{15}$ alcohols benzoate and sufficient cyclomethicone to provide 100 percent by weight.

2. A method as defined in claim 1 wherein 0.3 ml of the composition is applied once daily to the scalp with a rubbing action.

* * * * *